(12) United States Patent
Wu et al.

(10) Patent No.: US 6,572,693 B1
(45) Date of Patent: Jun. 3, 2003

(54) AESTHETIC DENTAL MATERIALS

(75) Inventors: Dong Wu, Woodbury, MN (US); Brian N. Holmes, St. Paul, MN (US); Brant U. Kolb, Afton, MN (US); Sumita B. Mitra, West St. Paul, MN (US); Wendy L. Thompson, Roseville, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 29 days.

(21) Appl. No.: 09/698,986

(22) Filed: Oct. 27, 2000

Related U.S. Application Data

(63) Continuation-in-part of application No. 09/428,830, filed on Oct. 28, 1999, now abandoned, which is a continuation-in-part of application No. 09/429,185, filed on Oct. 28, 1999, now Pat. No. 6,387,981, which is a continuation-in-part of application No. 09/428,937, filed on Oct. 28, 1999, now abandoned, which is a continuation-in-part of application No. 09/428,374, filed on Oct. 28, 1999, now Pat. No. 6,376,590.

(51) Int. Cl.$^7$ ................................................. A61K 7/00

(52) U.S. Cl. ........................ 106/35; 523/113; 523/115; 523/116

(58) Field of Search ............................ 106/35; 523/113, 523/115, 116

(56) References Cited

U.S. PATENT DOCUMENTS

| | | |
|---|---|---|
| 2,984,628 A | 5/1961 | Alexander et al. |
| 3,018,262 A | 1/1962 | Schroeder |
| 3,066,112 A | 11/1962 | Bowen ........................ 523/116 |
| 3,117,099 A | 1/1964 | Proops et al. |
| 3,422,817 A | 1/1969 | Luebke |
| 3,514,252 A | 5/1970 | Levy, Jr. et al. |
| 3,539,533 A | 11/1970 | Lee et al. |
| 3,629,187 A | 12/1971 | Waller |
| 3,708,296 A | 1/1973 | Schlesinger |
| 3,709,706 A | 1/1973 | Sowman |
| 3,709,866 A | 1/1973 | Waller |
| 3,729,313 A | 4/1973 | Smith |
| 3,741,769 A | 6/1973 | Smith |
| 3,751,399 A | 8/1973 | Lee et al. |
| 3,766,132 A | 10/1973 | Lee et al. |
| 3,808,006 A | 4/1974 | Smith |
| 3,860,556 A | 1/1975 | Taylor |
| 4,002,669 A | 1/1977 | Gross et al. |
| 4,069,055 A | 1/1978 | Crivello |
| 4,071,424 A | 1/1978 | Dart et al. |
| 4,115,346 A | 9/1978 | Gross et al. |
| 4,216,288 A | 8/1980 | Crivello |
| 4,250,053 A | 2/1981 | Smith |
| 4,250,311 A | 2/1981 | Crivello |
| 4,259,117 A | 3/1981 | Yamauchi et al. |
| 4,292,029 A | 9/1981 | Craig et al. |
| 4,308,190 A | 12/1981 | Walkowiak et al. .......... 106/35 |
| 4,327,014 A | 4/1982 | Kawahara et al. |
| 4,379,695 A | 4/1983 | Orlowski et al. |
| 4,387,240 A | 6/1983 | Berg .......................... 523/116 |
| 4,389,497 A | 6/1983 | Schmitt et al. .............. 523/116 |
| 4,394,403 A | 7/1983 | Smith |
| 4,404,150 A | 9/1983 | Tsunekawa et al. |
| 4,427,799 A | 1/1984 | Orlowski et al. ............ 523/116 |
| 4,503,169 A | 3/1985 | Randklev |
| 4,544,359 A | 10/1985 | Waknine ...................... 523/115 |
| 4,545,924 A | 10/1985 | Ritter, II |
| 4,612,138 A | 9/1986 | Keiser |
| 4,617,327 A | 10/1986 | Podszun |
| 4,619,817 A | 10/1986 | Stambaugh et al. |
| 4,642,126 A | 2/1987 | Zador et al. |
| 4,649,165 A | 3/1987 | Kuhlmann .................. 523/116 |
| 4,652,274 A | 3/1987 | Boettcher et al. |
| 4,661,540 A | 4/1987 | Le et al. |
| 4,696,955 A | 9/1987 | Kuhlmann .................... 522/77 |
| 4,719,091 A | 1/1988 | Wusirika |
| 4,737,593 A | 4/1988 | Ellrich et al. |
| 4,746,685 A | 5/1988 | Masuhara et al. |
| 4,769,351 A | 9/1988 | Soumiya et al. |
| 4,772,511 A | 9/1988 | Wood et al. |
| 4,772,530 A | 9/1988 | Gottschalk et al. |
| 4,778,671 A | 10/1988 | Wusirika |
| 4,784,794 A | 11/1988 | Kato |
| 4,868,288 A | 9/1989 | Meier |
| 4,874,450 A | 10/1989 | Gottschalk |
| 4,886,624 A | 12/1989 | Gradeff et al. |
| 4,923,905 A | 5/1990 | Masuhara et al. |
| 4,927,560 A | 5/1990 | Osaka et al. |
| 4,931,414 A | 6/1990 | Wood et al. |
| 4,946,665 A | 8/1990 | Recasens et al. |

(List continued on next page.)

FOREIGN PATENT DOCUMENTS

| | | |
|---|---|---|
| CA | 2202732 | 10/1997 |
| EP | 0 094 914 | 3/1986 |

(List continued on next page.)

OTHER PUBLICATIONS

Craig, "Restorative Dental Materials," 8$^{th}$ ed., 1989, p. 256.

C.W. Macosko, "Rheology Principles, Measurements, and Applications," VCH Publishers, Inc., New York, 1994, p. 92.

Surface 7 Colloid Science, vol. 6, ed. Matijevic, E., Wiley Interscience, 1973, pp. 23–29.

(List continued on next page.)

Primary Examiner—C. Melissa Koslow
(74) Attorney, Agent, or Firm—Doreen S. L. Gwin

(57) ABSTRACT

The invention provides for a material comprising (a) a hardenable resin; and (b) a filler comprising (i) clusters of nano-sized particles, the clusters comprising non-heavy metal oxide particles and heavy metal oxides, and being not fully densified particles and (ii) non-agglomerated nano-sized particles selected from the group consisting of non-heavy metal oxide particles, heavy metal oxide particles, and combinations thereof. The material is suitable for use as dental materials.

25 Claims, No Drawings

U.S. PATENT DOCUMENTS

| | | |
|---|---|---|
| 4,954,414 A | 9/1990 | Adair et al. |
| 4,985,229 A | 1/1991 | Obitsu et al. |
| 4,985,340 A | 1/1991 | Palazzotto et al. |
| 5,037,579 A | 8/1991 | Matchett .................. 252/313.1 |
| 5,055,372 A | 10/1991 | Shanklin et al. |
| 5,057,393 A | 10/1991 | Shanklin et al. |
| 5,073,476 A | 12/1991 | Meier et al. |
| 5,084,586 A | 1/1992 | Farooq |
| 5,089,536 A | 2/1992 | Palazotto |
| 5,124,417 A | 6/1992 | Farooq |
| 5,190,583 A | 3/1993 | Menzel et al. |
| 5,234,870 A | 8/1993 | Osaka et al. |
| 5,275,759 A | 1/1994 | Osaka et al. |
| 5,332,429 A | 7/1994 | Mitra et al. .................... 106/35 |
| 5,460,701 A | 10/1995 | Parker et al. |
| 5,470,910 A | 11/1995 | Spanhel et al. ............. 524/485 |
| 5,545,676 A | 8/1996 | Palazzotto et al. |
| 5,558,849 A | 9/1996 | Sharp |
| 5,593,781 A | 1/1997 | Nass et al. |
| 5,609,675 A | 3/1997 | Noritake et al. .............. 106/35 |
| 5,643,497 A | 7/1997 | Kaga et al. |
| 5,648,407 A | 7/1997 | Goetz et al. |
| 5,659,376 A | 8/1997 | Noguchi et al. |
| 5,698,483 A | 12/1997 | Ong et al. |
| 5,760,126 A | 6/1998 | Engle et al. |
| 5,776,239 A | 7/1998 | Bruno |
| 5,830,242 A | 11/1998 | Yao |
| 5,856,373 A | 1/1999 | Kaisaki et al. |
| 5,879,715 A | 3/1999 | Higgins et al. |
| 5,886,069 A | 3/1999 | Bolt |
| 5,935,275 A | 8/1999 | Burgard et al. |
| 5,936,006 A * | 8/1999 | Rheinberger et al. ....... 523/116 |
| 5,942,559 A | 8/1999 | Voser et al. |
| 6,025,406 A | 2/2000 | Oxman et al. |
| 6,063,830 A * | 5/2000 | Deguchi et al. ............ 523/115 |
| 6,136,886 A | 10/2000 | Deguchi ..................... 523/116 |
| 6,306,926 B1 * | 10/2001 | Bretscher et al. ........... 523/116 |

FOREIGN PATENT DOCUMENTS

| | | |
|---|---|---|
| EP | 0 173 567 | 3/1986 |
| EP | 0 184 467 A2 | 6/1986 |
| EP | 0 434 334 | 6/1991 |
| EP | 0 530 926 | 3/1993 |
| EP | 0 712 912 A2 | 5/1996 |
| EP | 0 841 304 A1 | 5/1998 |
| EP | 195 40 623 A1 | 5/1998 |
| GB | 2310855 | 9/1997 |
| JP | 3-46407 | 6/1984 |
| JP | 4-72768 | 9/1985 |
| JP | 9-194674 * | 7/1997 |
| WO | WO 93/05875 | 4/1993 |
| WO | WO 96/34829 | 11/1996 |
| WO | WO 98/13008 | 4/1998 |
| WO | WO 99/17716 * | 4/1999 |
| WO | WO 99/17716 | 12/1999 |
| WO | WO 99/65453 | 12/1999 |
| WO | WO 00/03688 | 1/2000 |
| WO | WO 00/20494 | 4/2000 |

OTHER PUBLICATIONS

W.B. Blumenthal, "The Chemical Behavior of Zirconium," D. Van Nostrand Company, Princeton, NJ, pp. 311–338.

"Perthometer, Surface Texture Parameters," Mahr GMB, Gottingen, Germany ed. Sep. 1, 1999, p. 10.

Patent Abstracts of Japan, vol. 1997, No. 11, Nov. 28, 1997; and JP 09/194674 A, Jul. 29, 1997 (Abstract).

"Routes To Deagglomerated Nanopowder By Chemical Synthesis"; Burgard et al.; *Mat. Res. Soc. Symp. Proc.*, vol. 346, 1994, pp. 101–107.

"Synthesis and Colloidal Processing of Nanocrystalline ($Y_2O_3$–Stabilized) $ZrO_2$ Powders by a Surface Free Energy Controlled Process"; Burgard, et al.; *Mat. Res. Soc. Symp. Proc.*, vol. 432, 1997, pp. 113–121.

"The Role of Complexing Ligants in the Formation of Non–Aggregated Nanoparticles of Zirconia"; Chatry et al.; *Journal of Sol–Gel Science and Technology*, vol. 1, 1994, pp. 233–240.

Japanese Patent Abstract for JP 1076919 A.
Japanese Patent Abstract for JP 1079015 A.
Japanese Patent Abstract for JP 1083518 A.
Japanese Patent Abstract for JP 1083519 A.
Japanese Patent Abstract for JP 1083520 A.
Japanese Patent Abstract for JP 1176225 A.
Japanese Patent Abstract for JP 2137729 A.
Japanese Patent Abstract for JP 2137730 A.
Japanese Patent Abstract for JP 2137731 A.
Japanese Patent Abstract for JP 2137732 A.
Japanese Patent Abstract for JP 3174326 A.
Japanese Patent Abstract for JP 4031307 A.
Japanese Patent Abstract for JP 4089319 A.
Japanese Patent Abstract for JP 7118016 A.
Japanese Patent Abstract for JP 8277114 A.
Japanese Patent Abstract for JP 9235119 A.
Japanese Patent Abstract for JP 58079818 A.
Japanese Patent Abstract for JP 58135131 A.
Japanese Patent Abstract for JP 59107969 A.
Japanese Patent Abstract for JP 60103033 A.
Japanese Patent Abstract for JP 60137827 A.
Japanese Patent Abstract for JP 60176920 A.
Japanese Patent Abstract for JP 60255622 A.
Japanese Patent Abstract for JP 61227917 A.
Japanese Patent Abstract for JP 61270217 A.
Japanese Patent Abstract for JP61141620 A.
Japanese Patent Abstract for JP 62065932 A.
Japanese Patent Abstract for JP 62091421 A.
Japanese Patent Abstract for JP 62128924 A.
Japanese Patent Abstract for JP 62212224 A.
Japanese Patent Abstract for JP 62226815 A.
Japanese Patent Abstract for JP 63002809 A.

Derwent Publications Ltd., Abstract for Japanese Pat. No. 54 077776 A, Jun. 21, 1979.

"Determination of Polymerization Shrinkage Kinetics in Visible–Light–Cured Materials: Methods Development" Dental Materials, Oct. 1991, pp. 281–286.

Definition of "binary compound," Oct. 09, 1997, [retrieved on Feb. 16, 2001] Retrieved from the 201 On–line Medical Dictionary using Internat<URL: http:/www.graylab.ac.uk/cgi–bin/omd?binary+compound>, 1 page.

Definition of "oxide," Oct. 09, 1997, [retrieved on Feb. 16, 2001] Retrieved from the © On–line Medical Dictionary using Internat <URL: http://www.graylab.ac.uk./cgi–bin/omd?oxide>, 1 page.

*Grant and Hackh's Chemical Dictionary*, 5th Edition, Dr. Roger Grant, Ed., Title Page, Publication Page, p. 106 and p. 231 (1987).

U.S. application Ser. No. 09/168,051, entitled Radiopaque Cationically Polymerizable Compositions Comprising a Radiopacifying Filler, and Method for Polymerizing Same, filed Oct. 7, 1998.

U.S. application Ser. No. 09/428,937, entitled Dental Materials with Nano–Sized Silica Particles, filed Oct. 28, 1999.

U.S. application Ser. No. 09/429,185, entitled Radiopaque Dental Materials with Nano–Sized Particles, filed Oct. 28, 1999.

U.S. application Ser. No. 09/428,374, entitled Zirconia Sol and Process of Making Same, filed Oct. 28, 1999.

Cabot Corporation Product Brochure, "Cab–O–Sil™ Untreated Fumed Silicia Properties and Functions," Title page, Publication page, and pp. 3–5 (1978).

Degussa AG Product Brochure, "Technical Bulletin Pigments, AEROSIL™ as a Thickening Agent for Liquid Systems," No. 23, Title page, Publication page, and pp. 3 and 29 (Jul. 1989).

Degussa AG Product Brochure, "Technical Bulletin Pigments, AEROSIL™ in Pharmaceuticals and Cosmetics," No. 49, Title page, Publication page, and pp. 5 and 6 (Sep. 1997).

U.S. patent application Ser. No. 09/168,051 "Radiopaque Cationically Polymerizable Compositions Comprising a Radiopacifying Filler, and Method for Polymerizaing Same-"filed Oct. 7, 1998.

* cited by examiner

AESTHETIC DENTAL MATERIALS

CROSS REFERENCE TO RELATED APPLICATIONS

This patent application is a continuation-in-part of U.S. Ser. Nos. 09/428,830, now abandoned; 09/429,185; now abandoned 09/428,937; 09/428,374, U.S Pat. No. 6,376, 590 all filed on Oct 28, 1999, which are hereby incorporated by reference in their entirety.

TECHNICAL FIELD

The present invention relates to fillers useful for aesthetic dental materials. In particular, the filler is a combination of nano-sized particles and clusters of nano-sized particles, where the former, due to their size and shape, reside in the interstitial spaces between the clusters.

BACKGROUND

Dental materials have special requirements. For health reasons, dental materials should be suitable for use in the oral environment. In certain applications, strength and durability of a dental material is important to ensure satisfactory performance. For example, for dental work at locations where mastication forces are generally great, high strength and durability is desirable. In other applications, an aesthetic character (e.g., luster and translucency) is desired. This is often the case where dental work is performed at locations where a tooth repair or restoration can be seen from a relatively short distance.

Strength in a dental material is typically achieved by adding fillers. Generally, a dental material has greater mechanical strength when it contains fillers having an average diameter greater than 0.4 to 0.6 micrometers. A disadvantage to these dental materials, however, is their tendency to lack luster and aesthetic character. Another disadvantage of composites with such average particle size is that with repeated toothbrushing (a requirement for oral hygiene), the hardened resin can wear away leaving a dull, unaesthetic surface. The worn surface can be a site for subsequent plaque accumulation.

Some skilled in the art have investigated using a combination of different average particle size fillers to improve the aesthetic character of the dental material.

For example, U.S. Pat. No. 5,936,006 (Rheinberger et al.) discloses a filled and polymerizable dental material characterized in that it contains a sol of amphorous $SiO_2$ particles in a liquid, organic dispersion agent, the $SiO_2$ particles being organically surface modified, having an average size of 10 to 100 nm and being non-agglomerated. The sol is referred to as "silica organosol (a)." The $SiO_2$ particles of the silica organosol (a) are organically modified at the surface. The dental material can also contain at least one polymerizable organic binder (b), and can contain conventional inorganic or organic particle-shaped fillers (c).

WO 00/03688 provides a dental enamel material having an opacity less than 50 percent and localized wear volume loss less than 0.025 $mm^3$. The material comprises a polymerizable matrix forming liquid having a first refractive index ($N_D$) and inorganic filler particles having a second $N_D$. The first $N_D$ is within 5 percent of the second $N_D$. The filler comprises particles of (a) low median particle size between 0.1 and 1.0 micrometers and (b) high median particle size between 1 and 10 micrometers. Preferred filler material is radiopaque dental glass such as barium aluminum-borosilicate glass, barium aluminofluorosilicate glass, and mixtures thereof. It is stated that the dental enamel material exhibits similar or improved physical characteristic when compared to known dental composites. Such physical characteristics include, among other things, opacity improvements, diametral tensile strength, polymerization shrinkage, and wear.

WO 99/65453 provides a dental composite comprising a resin base and a structural filler of ground particles having an average particle size between 0.05 and 0.5 micrometer. It is explained that because the structural filler particles are ground, they are non-spherical, providing increased adhesion of the resin to the structural filler. This increased adhesion is said to enhance the overall strength of the composite. The dental composite is said to provide the luster and translucency required for cosmetic applications. The structural filler is ground, typically by agitator milling, to the preferred mean particle size. This grinding-method is distinguished from the sol-gel process, in that the grinding method results in non-spherical particles.

Although the foregoing technology may provide useful dental materials, other compositions are sought.

SUMMARY

The present invention provides a dental material having a unique combination of filler particles: nano-sized particles and clusters of nano-sized particles (often referred to as "clusters" for convenience). It has been discovered that this combination provides a syngeristic effect that results in enhanced performance, as shown by the properties, of the inventive material. It is currently believed, as shown by transmission electron microscopy, that the smaller nano-sized particles fill the interstitial spaces between the larger clusters thereby minimizing voids in the composite dental material.

In brief summary, the inventive material comprises (a) a hardenable resin; and (b) a filler comprising (i) clusters of nano-sized particles, the clusters comprising non-heavy metal oxide particles and heavy metal oxides, and being not fully densified particles and (ii) non-agglomerated nano-sized particles selected from the group consisting of non-heavy metal oxide particles, heavy metal oxide particles, and combinations thereof. Preferably, the inventive material comprises a filler comprising at least about 60% by weight of the clusters and at most about 40% by weight of the nano-sized particles, based on the total filler. The material is a dental material.

In brief summary, the inventive material comprises (a) a hardenable resin; and (b) fillers comprising (i) clusters of nano-sized particles, the clusters comprising non-heavy metal oxide particles and heavy metal oxides, and being not fully densified particles; (ii) non-agglomerated nano-sized particles selected from the group consisting of non-heavy metal oxide particles, heavy metal oxide particles, and combinations thereof. The material is a dental material.

A method of making the inventive dental material comprises the acts of: (a) providing a hardenable resin; (b) providing a powder of filler particles comprising (i)-clusters of nano-sized particles, the clusters comprising non-heavy metal oxide particles and heavy metal oxides, and being not fully densified and (ii) non-agglomerated nano-sized particles selected from the group consisting of non-heavy metal oxide particles, heavy metal oxide particles, and combinations thereof, (c) surface treating the filler particles to yield surface-treated filler particles; and (d) mixing the surface treated filler particles with the hardenable resin.

A method of making the inventive dental material comprises the acts of: (a) providing a hardenable resin; (b)

providing a powder of filler particles comprising (i) clusters of nano-sized particles, the clusters comprising non-heavy metal oxide particles and heavy metal oxides, and being not fully densified; (ii) non-agglomerated nano-sized particles selected from the group consisting of non-heavy metal oxide particles, heavy metal oxide particles, and combinations thereof, (c) surface treating the filler particles to yield surface-treated filler particles; and (d) mixing the surface treated filler particles with the hardenable resin.

The clusters provide, among other things, strength while the nano-sized particles provide, among other properties, aesthetic quality, polishability, and wear resistance to the inventive material. Although the clusters and the nano-sized particles are structurally different types of fillers, they can have similar chemical constituents. Depending on the composition of the clusters and resin, one can add nano-sized non-heavy metal oxide particles, and/or heavy metal oxide particles to optimize the visual opacity and other properties of the inventive material. In this way, the present invention allows for flexibility in matching the refractive index of the components to minimize visual opacity. As a result, the inventive material exhibits excellent aesthetic quality while providing desirable properties. Such properties include, but are not limited to, good tensile strength, compressive strength, polishability, wear or abrasion resistance, luster, and low shrinkage after cure. Although low visual opacity is typically a desired property, it is not necessary for posterior applications.

The inventive material can be used in dental applications. Such applications include dental adhesives, artificial crowns, anterior or posterior fillings, casting materials, cavity liners, cements, coating compositions, mill blanks, orthodontic devices and adhesives, restoratives, prostheses, and sealants. The materials can be placed in the mouth and cured or hardened in situ. Alternatively, it may be fabricated into a prosthesis outside the mouth and subsequently adhered in place in the mouth.

DEFINITIONS

As used herein,

"Aesthetic quality" of a material, particularly a dental material, tends to be a subjective characteristic and yet a well-understood property in the dental industry. It can be quantified by visual opacity and/or polishability.

"Hardenable" is descriptive of a material that can be cured or solidified e.g., by heating to remove solvent, heating to cause polymerization, chemical crosslinking, radiation-induced polymerization or crosslinking, or the like;

"Non-heavy metal oxide" means any oxide of elements other than those of heavy metals.

"Polishability" is a property that can influence a material's aesthetic quality. Polishability is a measure of the retained gloss, i.e., polish retention and luster of a material after repeated abrasive contact, such as after tooth brushing.

"Visual opacity" is a property that can influence a material's aesthetic quality. In general, a low the visual opacity value is desirable.

DETAILED DESCRIPTION OF THE INVENTION

The components of the inventive material include fillers dispersed in a hardenable resin. Based on the total weight of the inventive material, the filler can be present at any amount, preferably at least 60%, more preferably at least 70%, and most preferably at least 75% by weight. Each component of the inventive material is discussed below in detail. As used in this document, the term "about" is presumed to preceed every recitation of a numeric value.

Filler Particles

The present invention provides for a combination of filler particles: clusters of nano-sized particles and non-agglomerated nano-sized particles. The clusters contains non-heavy metal oxide particles and heavy metal oxide. The nano-sized particles, on the other hand, generally tend to be discrete particles, and they can be non-heavy metal oxide particles and/or heavy metal oxide particles. The average diameter of the clusters, on a volumetric basis, is less than 10 micrometer, preferably less than 1 micrometer. The average diameter of the nano-sized particles, preferably based on TEM, is less than 200 nm, preferably less than 100 nm, more preferably less than 50 nm, and most preferably less than 20 nm. Each type of filler particles are discussed below in detail, first, the clusters, followed by the nano-sized particles.

The clusters are substantially amorphous in structure. The term "cluster" refers to the nature of the association among the non-heavy metal oxide particles in the cluster. Typically, the non-heavy metal oxide particles are associated by relatively weak intermolecular forces that cause them to clump together, i.e., to aggregate, even when dispersed in a hardenable resin. The heavy metal oxides can be present in various forms (as described in detail below). But, when they are present in the cluster as particles, the heavy metal oxide particles may display a similar association to each other and to the non-heavy metal oxide particles. By "substantially amorphous," it is meant that the clusters are essentially free of crystalline structure. The crystallinity of a material can be determined by a procedure that provides a Crystallinity Index (CI). A value of 1.0 on the CI indicates a fully crystalline structure, and a value near zero indicates predominantly amorphous phase. The clusters preferably have a CI of less than 0.2, more preferably less than 0.1, most preferably less than 0.05, according to x-ray diffraction methods.

Unlike conventional filler particles, the clusters are not fully densified. The phrase "fully densified," describes a particle that is near theoretical density, having substantially no open porosity detectable by standard analytical techniques. One useful technique is the Brunauer-Emmet-Tell (BET) method, which is described by S. J. Gregg and K. W. S. Sing in *Adsorption, Surface Area, and Porosity*, (Academic Press, London, 1982). The BET method uses nitrogen adsorption to determine the surface area of the particles, thereby giving an indication of porosity. Such measurements may be made on a QUANTASORB apparatus made by Quantachrome Corp., Syossett, N.Y. Density measurements may be made using an air, helium or water pycnometer.

The clusters can be made using a process that includes heat treatment. The clusters gain surface area after heat treatment. The ratio of the surface area after heat treatment compared to the surface area before heat treatment is preferably greater than 50%, more preferably greater than 80%.

Now turning to the chemical constituents of the clusters, they comprise non-heavy to metal oxide particles and heavy metal oxides.

First, the non-heavy metal oxide particles have an average diameter of less than 100 nanometer (nm), preferably less than 50 nm. These dimensions are preferably based on a TEM method, where one analyzes a population of particles to determine the average particle diameter. Such particles are preferably substantially spherical and substantially nonporous.

Suitable and useful non-heavy metal oxide particles include, e.g., silica, calcium phosphate, titanium oxide, feldspar, aluminum oxide, and the like. Silica, including its various forms such as fumed silica, colloidal silica, or aggregated silica particles, is preferred. Although the silica is preferably essentially pure, it may contain small amounts of stabilizing ion such as ammonium and alkaline metal ions.

Silica particles are preferably obtained from an aqueous silica colloidal dispersion (i.e., a silica sol or aquasol). In the silica sol, typically 1 to 50 weight percent is colloidal silica. Useful silica sols are those supplied as an aqueous dispersion of amorphous silica (such as the Nalco colloidal silicas made by Nalco Chemical Co., Naperville, Ill.) and those low in sodium concentration and can be acidified with a suitable acid (e.g., LUDOX colloidal silica made by E. I. DuPont de Nemours & Co., Wilmington, Del.). The silica particles in the sol have an average particle diameter of 5 to 100 nm, preferably 10 to 50 nm, more preferably 12 to 40 nm. Useful silica sols include NALCO 1040, 1042, 1050, and 1060, all commercially available from Nalco Chemical Co.

The second chemical constituent in the clusters is the heavy metal oxide, which imparts radiopacity to the inventive material. The term "radiopacity" describes the ability of the inventive material, after hardened, to be distinguished from tooth structure using standard dental X-ray equipment. The desired degree of radiopacity can be varied, depending upon the particular application and the expectations of the practitioner evaluating the X-ray film.

Useful heavy metal oxides contain metals having an atomic number greater than 28, preferably greater than 30, more preferably greater than 30 but less than 72. The heavy metal oxide should be chosen such that undesirable colors or shades are not imparted to the hardened resin in which it is dispersed. For example, iron and cobalt would not be favored, as they impart dark and contrasting colors to the tooth color. Suitable metal oxides are the oxides of yttrium, strontium, barium, zirconium, hafnium, niobium, tantalum, tungsten, bismuth, molybdenum, tin, zinc, lanthanide elements (i.e., elements having atomic numbers ranging from 57 to 71, inclusive), cerium, and combinations thereof. Preferred heavy metal oxides are oxides of lanthanum, zinc, tin, zirconium, yttrium, ytterbium, barium, strontium, cerium, and combinations thereof.

The heavy metal oxide component, as well as other additives, may exist in the inventive materials various forms. For example, they can be particles on the surface of the non-heavy metal oxide, particles amongst the non-heavy metal oxide or as a coating on at least a portion of the surface of a non-heavy metal oxide. Alternatively, the heavy metal oxide may be present in the non-heavy metal oxide particle as a solid solution (e.g., continuous glass) or a precipitate (a second phase).

Preferably, the heavy metal oxide is provided in the form of particles. When in particle form, the heavy metal oxide particles have an average diameter of less than 100 nm, preferably less than 50 nm, more preferably less than 10 nm. The heavy metal oxide particles may be aggregated. If so, the aggregated particles are less than 100 nm, and preferably are less than 50 nm in average diameter.

The heavy metal oxide is made from a precursor. Useful precusors can be organic or inorganic acid or water soluble salts, such as the heavy metal salts of aliphatic mono- or dicarboxylic acids (e.g. formic, acetic, oxalic, citric, tartaric, and lactic acids). Preferred precursors contain zirconium. Useful inorganic zirconium compounds include zirconium oxynitrate, zirconium acetate, and zirconium oxychloride. See U.S. Pat. No. 3,709,706, column 4, line 61, to column 5, line 5, for further details on zirconia sources that can be used in this invention. Zirconyl acetate compounds are preferred, particularly zirconyl acetate from MEI (Magnesium Elektron, Flemington, N.J.).

The clusters are prepared from a suitable non-heavy metal oxide sol and one or more heavy metal oxide precursor, which may be salts, sols, solutions, or nano-sized particles. Of these, sols are preferred. The term "sol" means a stable dispersion of colloidal solid particles within a liquid. The solid particles are typically denser than the surrounding liquid and small enough so that the dispersion forces are greater than the gravitational force. The particles are of a sufficiently small so that they generally do not refract visible light. Judicious choice of the precursor sols leads to desired degree of visual opacity and strength. The choice of the sol may depend on the following properties. The average size of the individual particles is preferably less than 100 nm in diameter. The acidity or the pH of the sol should preferably be below 6 and more preferably below 4. And, the sol should be free of impurities that cause undue aggregation (during the filler preparation process) of the individual discrete particles, during the subsequent steps, such as spray drying or calcining. If the starting sol is basic, it should be acidified, e.g., by adding nitric or other suitable acid to decrease the pH. Choosing a basic starting sol is less desirable because it requires an additional step and may lead to the introduction of undesired impurities. Typical impurities that are preferably avoided are metal salts, particularly salts of alkaline metals, e.g., sodium.

Prior to mixing the non-heavy metal oxide sol with the heavy metal oxide precursor, the pH of the non-heavy metal oxide sol is preferably reduced to provide an acidic solution having a pH of 1.5 to 4.0.

Once pH adjusted, the non-heavy metal sol and heavy metal oxide precursors are mixed together at a molar ratio to match the refractive index of the hardenable resin. This matching of refractive index imparts a low visual opacity. Preferably, the molar ratio ranges of non-heavy metal oxide ("non-HMO") to heavy metal oxide ("HMO"), expressed as non-HMO:HMO, is 0.5:1 to 10:1, more preferably 3:1 to 9:1, and most preferable 4:1 to 7:1. In a preferred embodiment where the clusters contain silica and zirconium, the method of preparation starts with a mixture of silica sol and zirconyl acetate, at a 5.5:1 molar ratio.

During mixing of the non-heavy metal oxide sol with the heavy metal oxide precursor, vigorous agitation is preferably used. After thorough mixing, the solution is dried to remove water and other volatile components to yield intermediate particles. Drying can be accomplished in various ways, including, e.g., tray drying, fluidized bed drying, and spray drying. In the preferred method where zirconyl acetate is used as the heavy metal precursor, spray drying is used with a 120° C. outlet temperature. Such a process removes water and acetic acid.

The intermediate particles are preferably made up of small, substantially spherical particles and hollow spheres. They are calcined to further remove residual organics to yield clusters. The calcining step increases the brittleness of the particles. In general, brittle particles tend to be easier to reduce in size. During calcining, the soak temperature is preferably 200° C. to 800° C., more preferably 300° C. to 600° C. Soaking is performed for 0.5 to 8 hours, depending on the amount of material being calcined. It is preferred that the soak time of the calcine step be such that a plateaued surface area is obtained. It is preferred that the time and temperature be chosen such that the resulting clusters are white in color, free from black, grey, or amber colored particles, as determined by visual inspection.

The calcined material is then preferably milled to a median particle size of less than 5 microns, preferably less than 2 microns (on a volumetric basis), as determined using a Sedigraph 5100 (Micrometrics, Norcross, Ga.). The particle size determination is performed by first obtaining the specific density of the filler using an Accupyc 1330 Pycometer (Micrometrics, Norcross, Ga.) described in the Test Methods. Milling can be accomplished by various methods including for example, stirred milling, vibratory milling, fluid energy milling, jet milling and ball milling. Ball milling is the preferred method.

The second type of filler particles is the nano-sized particles, which can be non-heavy metal oxide particles and/or heavy metal oxide particles. Suitable and useful materials for non-heavy metal oxide nano-sized particles and heavy-metal oxide particles can, and preferably are, the ones described above for the clusters. The heavy metal oxide nano-sized particles can be crystalline or non-crystalline, the former being preferred. Unlike the clusters, however, the when the nano-sized particles is a heavy metal oxide, such oxide takes on a particle form. The nano-sized particles are preferably substantially spherical and substantially non-porous.

Once dispersed in the resin, the non-heavy metal oxide nano-sized particles are in a discrete (individual) and unassociated (i.e. non-agglomerated, non-aggregated) condition. This condition is different from the clusters, which tend to remain agglomerated and/or aggregated. Once dispersed in the resin, the heavy-metal oxide nano-sized particles are in a non-agglomerated condition. The heavy-metal oxide nano-sized particles can be aggregates having an average diameter of less than 100 nm, preferably less than 75 nm. The term "agglomerated" means a weak association of particles usually held together by charge or polarity and can be broken down into smaller entities. The term "aggregated" means a strong association of particles often bound together by, e.g., residual chemical treatment. Further breakdown of the aggregates into smaller entities is difficult to achieve.

Silica is the preferred nano-sized non-heavy metal oxide particle. Although the silica is preferably essentially pure, it may contain small amounts of stabilizing ion such as ammonium and alkaline metal ions. Preferred and commercially available silica nano-sized particles are from Nalco Chemical Co. (Naperville, Ill.) under the product designation NALCO 2326, 2327, and 2329.

Zirconia is the preferred nano-sized heavy metal oxide particle. U.S. Pat. No. 5,037,579 (Matchett) discloses a suitable and preferred zirconia, which is typically non-agglomerated.

Another useful method of making zirconium oxide is disclosed in U.S. application Ser. No. 09/428,374 entitled "Zirconia Sol and Method of Making Same", now U.S. Pat. No. 6,376,590. The application discloses zirconia sols comprising an aqueous phase having dispersed therein a plurality of single crystal zirconia particles having an average primary particle size less than 20 nm, preferably ranging from 7 to 20 nm. The zirconia sols are substantially non-associated (i.e., non-aggregated and non-agglomerated) having a dispersion index ranging from 1 to 3, preferably ranging from 1 to 2.5, and more preferably ranging from 1 to 2. The zirconia sols are highly crystalline exhibiting a CI of 0.65 or greater, preferably 0.75 or greater, and more preferably 0.85 or greater. Of the crystalline phase, 70% or greater, preferably 75% or greater, and more preferably 85% or greater exists in combined cubic and tetragonal crystal lattice structures.

A method of making a zirconia sol is also disclosed. The method comprises the steps of: (a) providing an aqueous solution comprising a polyether acid zirconium salt; and (b) hydrolyzing the aqueous solution of the polyether acid zirconium salt by heating the solution at a temperature and a pressure sufficient to convert the polyether acid zirconium salt into crystalline zirconia particles. In a preferred method, step (a) comprises: (i) reacting an aqueous solution of a zirconium salt with a polyether carboxylic acid to form an aqueous solution comprising a polyether acid zirconium salt and a free acid; and (ii) optionally, removing at least a portion of the free acid. In a preferred embodiment, the step of removing at least the free acid comprises (a) drying an aqueous solution of the polyether acid zirconium salt; and (b) dispersing the dried acid polyether acid zirconium salt in water to form an aqueous solution.

Preferred zirconium salts for use as starting materials in the formation of a polyether acid zirconium salt have the general formula:

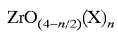

where X is a carboxylic acid displaceable counterion selected from the group consisting of formate, propionate, nitrate, chloride, carbonate and a combination thereof; and where n ranges from 0.5 to 4. A particularly preferred starting material is zirconium acetate.

Preferred polyether carboxylic acids for use in the process of the present invention have the general formula:

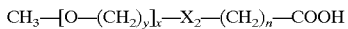

where $X_2$ is selected from the group consisting of:

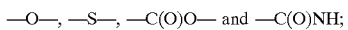

n ranges from 1 to 3;

x ranges from 1 to 10; and y ranges from 1 to 4. Examples of particularly preferred polyether carboxylic acids include 2-[2-(2-methoxyethoxy)ethoxy] acetic acid and 2-(2-methoxyethoxy) acetic acid.

Miscellaneous Components

The inventive material may optionally comprise additional adjuvants suitable for use in the oral environment, including colorants, flavorants, anti-microbials, fragrance, stabilizers, viscosity modifiers and fluoride releasing materials. For example, a fluoride releasing glass may be added to the materials of the invention to provide the benefit of long-term release of fluoride in use, for example in the oral cavity. Fluoroaluminosilicate glasses are particularly preferred. Particularly preferred are silanol treated fluoroaluminosilicate glass fillers, as described in U.S. Pat. No. 5,332,429, the disclosure of which is expressly incorporated by reference herein. Other suitable adjuvants include agents that impart fluorescence and/or opalescence. Optionally, fumed silica can be used. Suitable fumed silicas include for example, products sold under the tradename AEROSIL series OX-50, -130, -150, and -200 available from DeGussa AG, (Hanau, Germany), and CAB-O-SIL M5 available from Cabot Corp (Tuscola, Ill.).

Surface Treatment

The filler particles, i.e., clusters and nano-sized particles, can be surfaced treated before they are added to the resin to increase the probability of forming a stable dispersion. The term "stable" generally means that the filler particles do not agglomerate after standing for a period of time, such as 24 hours, under standard ambient conditions, e.g. room temperature (20° C. to 22° C.), atmospheric pressure, and no extreme electro-magnetic forces. Preferably, the surface treatment stabilizes the filler particles so that they are well dispersed in the hardenable resin yielding a substantially homogeneous composition. The term "surface treatment" is synonymous with surface modifying. The surface treatment for these various types of fillers are discussed below in detail.

The clusters are preferably treated with a resin-compatibilizing surface treatment agent. Particularly preferred surface treatment agents include silane treatment agents capable of polymerizing with a resin. Preferred silane treatment agents include γ-methacryloxylpropyl-trimethoxysilane, available under the trade designation A-174 from Witco OSi Specialties (Danbury, Conn.), γ-glycidoxypropyltrimethoxy silane, available under the trade designation G6720 from United Chemical Technologies (Bristol, Pa.), and styrylethyltrimethyloxysilane, available from Gelest Inc. (Tullytown, Pa.).

Alternatively a combination of surface treatment agents can be used, where at least one of the agents has a functional group co-polymerizable with the hardenable resin. For example, the polymerizing group can be ethylenically unsaturated or a cyclic function subject to ring opening polymerization. An ethylenically unsaturated polymerizing group can be, e.g., acrylates, methacrylates or vinyl groups. A cyclic function subject to ring opening polymerization generally contains a heteroatom such as oxygen, sulfur or nitrogen, and preferably is a 3-membered ring containing oxygen such as an epoxide. Other surface modifying agents that do not generally react with hardenable resins can be included to enhance dispersibility or rheological properties, such as, e.g., aryl polyethers, alkyl, hydroxyalkyl, hydroxyaryl, or aminoalkyl functional silanes.

The nano-sized particles are made by mixing the inorganic sol with surface modifying agents. Optionally, a co-solvent can be added at this point, such as for example, 1-methoxy propanol. The co-solvent can enhance the solubility of the surface modifying agents as well as the surface modified particles. The mixture comprising the inorganic sol and surface modifying agents is subsequently reacted at room or an elevated temperature, with or without mixing. In a preferred method, the mixture is reacted at 85° C. for 24 hours, resulting in the surface modified sol. In a preferred method, where the nano-sized particles are non-heavy metal oxide particles and heavy metal oxide particles, the surface treatment of the latter can preferably involve the adsorption of acidic molecules to the particle surface.

For the nano-sized heavy metal oxide particle, a preferred surface treatment agent contains functional groups that provide dispersibility and/or reactivity such particles within the desired hardenable resin. Preferably, the agent is an acidic compound. Suitable acids include, e.g., carboxylic acids, phosphonic acids, and sulfonic acids. More preferably, the surface treatment is done with a mixture of acidic compounds. Alternatively, a mixture of acidic compounds where at least one compound has a polymerizable functionality can be used. Most preferably, the acidic function is derived from oxyacids of boron, carbon, phosphorus, and sulfur. For example, it has been found that carboxylic acids adsorb particularly well to the surface of zirconia and ceria particles.

Preferably, the acids include the structure R—COOH, where R is an organic radical containing ethylenic unsaturation. R may be branched- or straight chained and may be substituted (e.g., by a heteroatom). R typically contains from 1 to 50 carbon atoms, preferably 2 to 20 carbon atoms. A particularly preferred group of such acids includes R groups with terminal ethylenic unsaturation.

Adsorption of a combination of acids to the surface of the nano-sized heavy metal oxide particles provides a desirable modification to impart strength, dispersibility, and stability of such particles in the resin. In a preferred method, nano-sized zirconia particles are dispersed in water with acetic acid adsorbed to the surface. The surface modification involves replacement of adsorbed acetic acid with a combination of acids chosen to provide good dispersion and high strength of the zirconia particles.

Suitable surface treatment agents include hydrophilic, non-reactive acids such as 2-[2-(2-methoxy)ethoxy]ethoxy acetic acid (MEEAA), mono(polyethyleneglycol)succinate, mono(polyethyleneglycol)maleate. These acids provide good dispersion of the nano-sized heavy metal oxide particles in the resin.

Strength in the inventive material can be enhanced via copolymerization of surface treating groups with the hardenable resin. Preferably, this is accomplished by using a reactive surface modifier. Examples of hydrophilic and reactive acids suitable for the surface treatment include 2-hydroxymethyl-2-[(N-methacryloxyethyl) carbamoylmethyl] propionic acid (PAMA), mono (acryloxypolyethyleneglycol)succinate, and mono (acryloxypolyethyleneglycol)maleate. Other suitable reactive acids include 2,2-bis[(N-methacryloxyethyl) carbamoylmethyl] propionic Acid (PDMA), acrylic acid, methacrylic acid, beta carboxyethylacrylate, mono-2-(methacryloxy)ethyl succinate, and mono-2-(methacryloxy) ethyl maleate.

Combinations of non-reactive and reactive acids are also desirable to impart organic compatibility and reactivity. Other suitable acid mixtures useful for surface treatment of the nano-sized heavy metal oxide particles include aliphatic carboxylic acids such as, e.g., oleic acid, stearic acid, and octanoic acid, aromatic nonreactive acids such as methoxy phenyl acetic acid and 3,4,5 triethoxy benzoic acid, as well as itaconic acid, toluene sulfonic acid, ethylene glycol methacrylate phosphate, the salts of the acids just stated, and blends thereof.

Dispersing the Filler Particles in the Resin

Once the filler particles have been surface treated, they can be added to the hardenable resin using various techniques.

The surface treated nano-sized particles can be added into the hardenable resin in various methods. In one aspect, a solvent exchange procedure is used where the resin is added to the surface modified sol, followed by removal of water and co-solvent s(if used) by evaporation, thus leaving the particles dispersed in the hardenable resin. The evaporation step can be accomplished, e.g., by distillation, rotary evaporation or oven drying.

One method for incorporating nano-sized particles into resin involves the drying of the surface modified nano-sized particles into a powder. The powder can be dispersed in the resin. The drying step can be accomplished by conventional means suitable for the system, such as, e.g., oven drying or spray drying. In spray drying, the inlet temperature is preferably at 200° C. and the outlet temperature is preferably between 85° C. to 100° C. In another aspect, conventional oven drying can be used at temperatures between 70° C to 90° C. for 2 to 4 hours.

In another method, the surface modified nano-sized particles can be filtered to obtain solids, which can be dried into a powder. This method is preferred when the particles of the surface modified aqueous sol have agglomerated due to the incompatibility of the surface treatment with the aqueous medium. The resin is then added to the dry, filtered particles.

As suggested above, the surface treated clusters can be supplied in dry powder form and resin can be added to the powder.

Hardenable Resins

To achieve low visual opacity, it is desirable to minimize the scattering of light as it passes through the inventive material. The resins useful for the inventive materials are generally thermosetting resins capable of being hardened to form a polymer network. Suitable resins include acrylate resins, methacrylate resins, epoxy resins, vinyl resins, and mixtures thereof. Preferably, the hardenable resin is made from one or more matrix-forming oligomer, monomer, or polymer, or blends thereof.

In a preferred embodiment where the inventive material is a dental composite, suitable polymerizable resins include hardenable organic resins having sufficient strength, hydrolytic stability, and non-toxicity to render them suitable for use in the oral environment. Examples of such resins include acrylate, methacrylate, urethane, carbamoylsiocyanurate, epoxy resins, and mixtures and derivatives thereof. U.S. Pat. Nos. 3,066,112, 3,539,533, 3,629,187, 3,709,866, 3,751,399, 3,766,132, 3,860,556, 4,002,669, 4,115,346, 4,259,117, 4,292,029, 4,308,190, 4,327,014, 4,379,695, 4,387,240 and 4,404,150 disclose such resins.

One class of preferred hardenable resins are materials having free radically active functional groups and include monomers, oligomers, and polymers having one or more ethylenically unsaturated groups. Alternatively, the hardenable resin can be a material from the class of resins that include cationically active functional groups. In another alternative, a mixture of hardenable resins that include both cationically curable and free radically curable resins may be used.

In the class of hardenable resins having free radically active functional groups, suitable materials for use in the invention contain at least one ethylenically unsaturated bond, and are capable of undergoing addition polymerization. Such free radically polymerizable materials include mono-, di- or poly-acrylates and methacrylates such as methyl acrylate, methyl methacrylate, ethyl acrylate, isopropyl methacrylate, n-hexyl acrylate, stearyl acrylate, allyl acrylate, glycerol diacrylate, glycerol triacrylate, ethyleneglycol diacrylate, diethyleneglycol diacrylate, triethyleneglycol dimethacrylate, 1,3-propanediol diacrylate, 1,3-propanediol dimethacrylate, trimethylolpropane triacrylate, 1,2,4-butanetriol trimethacrylate, 1,4-cyclohexanediol diacrylate, pentaerythritol triacrylate, pentaerythritol tetraacrylate, pentaerythritol tetramethacrylate, sorbitol hexacrylate, the diglycidyl methacrylate of bis-phenol A ("Bis-GMA"), bis[ 1-(2-acryloxy)]-p-ethoxyphenyldimethylmethane, bis[1-(3-acryloxy-2-hydroxy)]-p-propoxyphenyldimethylmethane, and trishydroxyethyl-isocyanurate trimethacrylate; the bis-acrylates and bis-methacrylates of polyethylene glycols of molecular weight 200 to 500, copolymerizable mixtures of acrylated monomers such as those in U.S. Pat. No. 4,652,274, and acrylated oligomers such as those of U.S. Pat. No. 4,642,126; and vinyl compounds such as styrene, diallyl phthalate, divinyl succinate, divinyl adipate and divinylphthalate. Mixtures of two or more of these free radically polymerizable materials can be used if desired.

For free radical polymerization (hardening), an initiation system can be selected from systems which initiate polymerization via radiation, heat, or redox/auto-cure chemical reaction. A class of initiators capable of initiating polymerization of free radically active functional groups includes free radical-generating photoinitiators, optionally combined with a photosensitizer or accelerator. Such initiators typically an be capable of generating free radicals for addition polymerization upon exposure to light energy having a wavelength between 200 and 800 nm.

A variety of visible or near-IR photoinitiator systems may be used for photopolymerization of free-radically polymerizable resin. For example, a photoinitiation system can be selected from systems which initiate polymerization via a two component system of an amine and an α-diketone as described in U.S. Pat. No. 4,071,424. Alternatively, the resin can be combined with a three component photoinitiator system such as described in U.S. Pat. No. 5,545,676 (Palazzotto et al.). The three component system includes an iodonium salt (i.e., a diaryliodonium salt), a sensitizer, and a donor. Each photoinitiator component is discussed in U.S. Pat. No. 5,545,676, column 2, line 27, to column 4, line 45.

Other useful free-radical initiators include the class of acylphosphine oxides, as described in European Pat. Application No. 173567, U.S. Pat. No. 4,737,593 and United Kingdom Patent No. GB 2,310,855. Such acylphosphine oxides are of the general formula

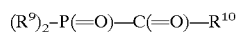

wherein each $R^9$ individually can be a hydrocarbyl group such as alkyl, cycloalkyl, aryl, and aralkyl, any of which can be substituted with a halo-, alkyl- or alkoxy-group, or the two $R^9$ groups can be joined to form a ring along with the phosphorous atom, and wherein $R^{10}$ is a hydrocarbyl group, an S-, O-, or N-containing five- or six-membered heterocyclic group, or a —Z—C(=O)—P(=O)—$(R^9)_2$ group, wherein Z represents a divalent hydrocarbyl group such as alkylene or phenylene having from 2 to 6 carbon atoms.

Preferred acylphosphine oxides useful in the invention are those in which the $R^9$ and $R^{10}$ groups are phenyl or lower alkyl- or lower alkoxy-substituted phenyl. By "lower alkyl" and "lower alkoxy" is meant such groups having from 1 to 4 carbon atoms. Most preferably, the acylphosphine oxide is bis(2,4,6-trimethylbenzoyl)phenyl phosphine oxide (IRGACURE™ 819, Ciba Specialty Chemicals, Tarrytown, N.Y.).

Tertiary amine reducing agents may be used in combination with an acylphosphine oxide. Illustrative tertiary amines useful in the invention include ethyl 4-(N,N-dimethylamino) benzoate and N,N-dimethylaminoethyl methacrylate. The initiator can be used in catalytically-effective amounts, such as from 0.1 to 5 weight percent, based on the weight of ethylenically-unsaturated compound present, of the acylphosphine oxide plus from 0.1 to 5 weight percent, based on the weight of ethylenically-unsaturated compound present, of the tertiary amine.

Commercially-available phosphine oxide photoinitiators capable of free-radical initiation when irradiated at wavelengths of greater than 400 to 1200 nm include a 25:75 mixture, by weight, of bis(2,6-dimethoxybenzoyl)-2,4,4-trimethylpentyl phosphine oxide and 2-hydroxy-2-methyl-1-phenylpropan-1-one (IRGACURE™ 1700, Ciba Specialty Chemicals), 2-benzyl-2-(N,N-dimethylamino)-1-(4- morpholinophenyl)-1-butanone (IRGACURE™ 369, Ciba Specialty Chemicals), bis($\eta^5$-2,4-cyclopentadien-1-yl)-bis (2,6-difluoro-3-(1H-pyrrol-1-yl)phenyl) titanium (IRGACURE™ 784 DC, Ciba Specialty Chemicals), a 1:1 mixture, by weight, of bis(2,4,6-trimethylbenzoyl)phenyl phosphine oxide and 2-hydroxy-2-methyl-1-phenylpropane-1-one (DAROCUR™ 4265, Ciba Specialty Chemicals), and ethyl-2,4,6-trimethylbenzylphenyl phosphinate (LUCIRIN™ LR8893X, BASF Corp., Charlotte, N.C.).

Another free-radical initiator system that can alternatively be used in the dental materials of the invention includes the class of ionic dye—counterion complex initiators comprising a borate anion and a complementary cationic dye. Borate salt photoinitiators are described, for example, in U. S. Pat. Nos. 4,772,530, 4,954,414, 4,874,450, 5,055,372, and 5,057,393. Borate anions useful in these photoinitiators generally can be of the formula $$R^1R^2R^3R^4B^-$$

wherein $R^1$, $R^2$, $R^3$, and $R^4$ independently can be alkyl, aryl, alkaryl, allyl, aralkyl, alkenyl, alkynyl, alicyclic and saturated or unsaturated heterocyclic groups. Preferably, $R^2$, $R^3$, and $R^4$ are aryl groups and more preferably phenyl groups, and $R^1$ is an alkyl group and more preferably a secondary alkyl group.

Cationic counterions can be cationicdyes, quaternary ammonium groups, transition metal coordination complexes, and the like. Cationic dyes useful as counterions can be cationic methine, polymethine, triarylmethine, indoline, thiazine, xanthene, oxazine or acridine dyes. More specifically, the dyes may be cationic cyanine, carbocyanine, hemicyanine, rhodamine, and azomethine dyes. Specific examples of useful cationic dyes include Methylene Blue, Safranine O, and Malachite Green. Quaternary ammonium groups useful as counterions can be trimethylcetylammonium, cetylpyridinium, and tetramethylammonium. Other organophilic cations can include pyridinium, phosphonium, and sulfonium. Photosensitive transition metal coordination complexes that may be used include complexes of cobalt, ruthenium, osmium, zinc, iron, and iridium with ligands such as pyridine, 2,2'-bipyridine, 4,4'-dimethyl-2,2'-bipyridine, 1,1 0-phenanthroline, 3,4,7,8-tetramethylphenanthroline, 2,4,6-tri(2-pyridyl-s-triazine) and related ligands.

Yet another alternative class of initiators capable of initiating polymerization of free radically active functional groups in the hardenable resin includes conventional chemical initiator systems such as a combination of a peroxide and an amine. These initiators, which rely upon a thermal redox reaction, are often referred to as "auto-cure catalysts." They are typically supplied as two-part systems in which the reactants are stored apart from each other and then combined immediately prior to use.

In a further alternative, heat may be used to initiate the hardening, or polymerization, of free radically active groups. Examples of heat sources suitable for the dental materials of the invention include inductive, convective, and radiant. Thermal sources should be capable of generating temperatures of at least 40° C. to 150° C. under normal conditions or at elevated pressure. This procedure is preferred for initiating polymerization of materials occurring outside of the oral environment.

Yet another alternative class of initiators capable of initiating polymerization of free radically active functional groups in the hardenable resin are those that include free radical-generating thermal initiators. Examples include peroxides such as, e.g., benzoyl peroxide and lauryl peroxide, and azo compounds such as, for example, 2,2-azobis-isobutyronitrile (AIBN).

Now returning to the hardenable resins, an alternative class of hardenable resins useful in the inventive material includes cationically active functional groups. Materials having cationically active functional groups include cationically polymerizable epoxy resins, vinyl ethers, oxetanes, spiro-orthocarbonates, spiro-orthoesters, and the like.

Preferred materials having cationically active functional groups are epoxy resins such as those disclosed in U.S. Pat. No. 6,025,406 (Oxman et al.) at column 2, line 36, to column 4, line 52.

Optionally, monohydroxy- and polyhydroxy-alcohols may be added to the hardenable resin, as chain-extenders for the epoxy resin. The hydroxyl-containing material used in the present invention can be any organic material having hydroxyl functionality of at least 1, and preferably at least 2.

Preferably the hydroxyl-containing material contains two or more primary or secondary aliphatic hydroxyl groups (i.e., the hydroxyl group is bonded directly to a non-aromatic carbon atom). The hydroxyl groups can be terminally situated, or they can be pendent from a polymer or copolymer. The molecular weight of the hydroxyl-containing organic material can vary from very low (e.g., 32) to very high (e.g., one million or more). Suitable hydroxyl-containing materials can have low molecular weights, i.e., from 32 to 200, intermediate molecular weight, i.e., from 200 to 10,000, or high molecular weight, i.e., above 10,000. As used herein, all molecular weights are weight average molecular weights.

The hydroxyl-containing material can optionally contain other functionalities that do not substantially interfere with cationic cure at room temperature. Thus, the hydroxyl-containing materials can be nonaromatic in nature or can contain aromatic functionality. The hydroxyl-containing material can optionally contain heteroatoms in the backbone of the molecule, such as nitrogen, oxygen, sulfur, and the like, provided that the ultimate hydroxyl-containing material does not substantially interfere with cationic cure at room temperature. The hydroxyl-containing material can, for example, be selected from naturally occurring or synthetically prepared cellulosic materials. Of course, the hydroxyl-containing material is also substantially free of groups which may be thermally or photolytically unstable; that is, the material will not decompose or liberate volatile components at temperatures below 100° C. or in the presence of actinic light which may be encountered during the desired curing conditions for the photocopolymerizable composition. Useful hydroxyl-containing materials are described, for example, in U.S. Pat. No. 5,856,373.

The amount of hydroxyl-containing organic material can vary over broad ranges, depending upon factors such as the compatibility of the hydroxyl-containing material with the epoxide, the equivalent weight and functionality of the hydroxyl-containing material, the physical properties desired in the final cured composition, the desired speed of photocure, and the like.

Blends of various hydroxyl-containing materials can be useful. Examples of such blends include two or more molecular weight distributions of hydroxyl-containing compounds, such as low molecular weight (below 200), intermediate molecular weight (200 to 10,000) and higher molecular weight (above 10,000). Alternatively or additionally, the hydroxyl-containing material can contain a blend of hydroxyl-containing materials having different chemical natures, such as aliphatic and aromatic, or functionalities, such as polar and non-polar. As an additional example, one may use mixtures of two or more polyfunctional hydroxy materials or one or more monofunctional hydroxy materials with poly-functional hydroxy materials.

For hardening resins comprising cationically active functional groups, an initiation system can be selected from systems which initiate polymerization via radiation, heat, or redox/auto-cure chemical reaction. For example, epoxy polymerization may be accomplished by the use of thermal curing agents, such as anhydrides or amines. A particularly useful example of an anhydride curing agent would be cis-1,2-cyclohexanedicarboxylic anhydride.

Alternatively and preferably, initiation systems for resins comprising cationically active functional groups are those that are photoactivated. The broad class of cationic photoactive groups recognized in the catalyst and photoinitiator industries may be used in the practice of the present invention. Photoactive cationic nuclei, photoactive cationic moieties, and photoactive cationic organic compounds are art recognized classes of materials as exemplified by U.S. Pat. Nos. 4,250,311; 3,708,296; 4,069,055; 4,216,288; 5,084,586; 5,124,417; 4,985,340, 5,089,536, and 5,856,373.

The cationically-curable materials can be combined with a three component or ternary photoinitiator system, as described above.

For hardening cationically curable resins, examples of useful aromatic iodonium complex salts are disclosed in U.S. Pat. No. 6,025,406, column 5, line 46, to column 6, line 9. Examples of useful sensitizer and electron donor can also be found in U.S. Pat. No. 6,025,406, column 6, line 43, to column 9, line 43.

An alternative photoinitiator system for cationic polymerizations includes the use of organometallic complex cations essentially free of metal hydride or metal alkyl functionality selected from those described in U.S. Pat. No. 4,985,340 and has the formula:

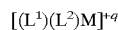

wherein

M represents a metal selected from the group consisting of Cr, Mo, W, Mn, Re, Fe, Ru, Os, Co, Rh, Ir, Pd, Pt and Ni, preferably Cr, Mo, W, Mn, Fe, Ru, Co, Pd, and Ni; and most preferably Mn and Fe;

$L^1$ represents 1 or 2 cyclic, polyunsaturated ligands that can be the same or different ligand selected from the group consisting of substituted and unsubstituted cyclopentadienyl, cyclohexadienyl, and cycloheptatrienyl, cycloheptatriene, cyclooctatetraene, heterocyclic compounds and aromatic compounds selected from substituted or unsubstituted arene compounds and compounds having 2 to 4 fused rings, and units of polymers, e.g., a phenyl group of polystyrene, poly(styrene-co-butadiene), poly(styrene-co-methyl methacrylate), poly(a-methylstyrene), and the like; a cyclopentadiene group of poly(vinylcyclopentadiene); a pyridine group of poly(vinylpyridine), and the like, each capable of contributing 3 to 8 electrons to the valence shell of M;

$L^2$ represents none, or 1 to 3 nonanionic ligands contributing an even number of electrons that can be the same or different ligand selected from the group of carbon monoxide, ketones, olefins, ethers, nitrosonium, phosphines, phosphites, and related derivatives of arsenic and antimony, organonitriles, amines, alkynes, isonitriles, dinitrogen, with the proviso that the total electronic charge contributed to M results in a net residual positive charge of q to the complex;

q is an integer having a value of 1 or 2, the residual charge of the complex cation.

Organometallic salts are known in the art and can be prepared as described in, for example, EPO No. 094,914 and U.S. Pat. Nos. 5,089,536, 4,868,288, and 5,073,476.

Examples of preferred cations include:

diphenyliodonium, ditolyliodonium, didodecylphenyliodonium, (4-octyloxyphenyl)phenyliodonium, and bis(methoxyphenyl)iodonium;

triphenylsulfonium, diphenyl-4-thiophenoxyphenylsulfonium, and 1,4-phenylene-bis(diphenylsufonium);

bis($\eta^5$-cyclopentadienyl)iron(1+), bis($\eta^5$-methylcyclopentadienyl)iron (1+), ($\eta$5-cyclopentadienyl)($\eta^5$-methylcyclopentadienyl)iron (1+), and bis($\eta^5$-trimethylsilylcyclopentadienyl)iron (1+);

bis($\eta^6$-xylenes)iron (2+), bis($\eta^6$-mesitylene)iron (2+), bis ($\eta^6$-durene)iron (2+), bis($\eta^6$-pentamethylbenzene)iron (2+), and bis($\eta^6$-dodecylbenzene) iron (2+);

($\eta^5$-cyclopentadienyl)($\eta^6$-xylenes)iron(1+), commonly abbreviated as (CpFeXy)(1+), ($\eta^5$-cyclopentadienyl)($\eta^6$-toluene)iron(1+), ($\eta^5$-cyclopentadienyl)($\eta^6$-mesitylene)iron(1+), ($\eta^5$-cyclopentadienyl)($\eta^6$-pyrene)iron(1+), ($\eta^5$-cyclopentadienyl)($\eta^6$-naphthalene)iron(1+), and ($\eta^5$-cyclopentadienyl)($\eta^6$-dodecylphenyl)iron(1+).

Alternatively, the hardenable resins may have both cationically active and free radically active functional groups contained in a single molecule. Such molecules may be obtained, e.g., by reacting a di- or poly-epoxide with one or more equivalents of an ethylenically unsaturated carboxylic acid. An example of such a material is the reaction product of UVR-6105 (available from Union Carbide) with one equivalent of methacrylic acid. Commercially available materials having epoxy and free-radically active functionalities include the CYCLOMER series, such as CYCLOMER M-100, M-101, or A-200 available from Daicel Chemical, Japan, and Ebecryl-3605 available from Radcure Specialties.

The photoinitiator compounds are preferably provided in the dental materials of the invention in an amount effective to initiate or enhance the rate of cure or hardening of the resin system. Photopolymerizable compositions useful in the invention are prepared by simply admixing, under safe light conditions, the components as described above. Suitable inert solvents may be used, if desired, when effecting this mixture. Any solvent may be used which does not react appreciably with the components of the inventive compositions. Examples of suitable solvents include acetone, dichloromethane, and acetonitrile. A liquid material to be polymerized may be used as a solvent for another liquid or solid material to be polymerized. Solventless compositions can be prepared by simply dissolving an aromatic iodonium complex salt and sensitizer in an epoxy resin-polyol mixture with or without the use of mild heating to facilitate dissolution.

In a preferred method of using the denial material of the invention, comprising a hardenable resin and fillers of the invention, the material is placed near or on a tooth surface, followed by a manipulation by the practitioner or laboratory to change the topography of the material, then hardening the resin. These steps can be followed sequentially or in a different order. For example, in a preferred embodiment where the dental material is a mill blank or a prosthesis, the hardening step is generally completed prior to changing the topography of the material. Changing the topography of the material can be accomplished in various ways, including manual manipulation using hand held instruments, or by machine or computer aided apparatus, such as a CAD/CAM milling machine in the case of prostheses and mill blanks Optionally, a finishing step can be performed to polish, finish, or apply a coating on the dental material.

Test Methods

Average Particle Diameter Determination

Samples approximately 80nm thick are placed on 200 mesh copper grids with carbon stabilized formvar substrates (SPI Supplies-a division of Structure Probe, Inc., West Chester, Pa.). A transmission electron micrograph (TEM) is taken, using JEOL 200CX (JEOL, Ltd. of Akishima, Japan and sold by JEOL USA, Inc.) at 200Kv. A population size of 50 to 100 particles can be measured and an average diameter is determined.

Cluster Size Determination

Cluster size distribution was determined by sedimentation techniques using a Sedigraph Model 5100 (Micrometrics, Norcross, Ga.). Specific density of the cluster was determined by using an Accupyc 1330 Pycometer (Micrometrics, Norcross, Ga.). A dispersant solution was prepared as follows. To 2880 g of water was added 8.0g of TWEEN 80 (Aldrich Chemical Co., Milwaukee, Wiss.), 3.2g sodium hexametaphosphate 66.8–68.0 assay (Matheson Coleman & Bell, Cincinnati, Ohio), 0.08g sodium fluoride (>99% assay, Aldrich Chemical Co., Milwaukee, Wiss.), 8.0g Liqui-Nox (Alconox, Inc., New York, N.Y.), and 320.0 g glycerol 99.5% by volume (Aldrich Chemical Co., Milwaukee, Wiss.). The pH of the solution was adjusted with the contents of 4 tablets from pHydration Capsules pH7.00 (Micro Essential Laboratory Inc., Brooklyn, N.Y.). An 80 ml portion of the above solution was added to the 5.0g of filler. The resultant slurry was sonicated for 9 minutes using a W-225 Sonicator Processor (Heat Systems Ultrasonics Inc., Farmingdale, N.Y.) with the output control knob set at 7, and the percent (%) Duty Cycle set at 70%. Cluster size distribution was determined by the Sedigraph Model 5100.

Visual Opacity Testing

Disc-shaped 1 mm thick by 20 mm diameter samples were cured using a Visilux 2™ unit (3M Co, St. Paul, Minn.) for 60 seconds on each side of the disk at a distance of 6 mm. The cured samples were then evaluated for visual opacity as follows. Cured samples were measured for direct light transmission by measuring transmission of light through the thickness of the disk using a MacBeth transmission densitometer Model TD-903 equipped with a visible light filter, available from MacBeth (MacBeth, Newburgh, N.Y.).

The inventive materials have a visual opacity of less than 0.35, or 0.05 to 0.5, preferably 05 to 0.35, more preferably 0.05 to 0.25, as measured using the MacBeth unit. By chosing suitable combinations of clusters, non-heavy metal oxide nano-sized particles, and heavy metal oxide nano-sized particles, the desired visual opacity can be achieved.

Diametral Tensile Strength (DTS)

DTS indicates a material's ability to withstand compression forces that introduce a tensile stress in the material. Hardened materials of the invention preferably have a diametral tensile strength of at least 15MPa; more preferably at least 40MPa; most preferably at least 60 MPa.

ADA ("American Dental Association") specification No. 9 was followed for DTS testing. Each sample was packed into a 4 mm inside diameter glass tube, capped with silicone rubber plugs and axially compressed at 0.28 MPa for 15 minutes, then light cured for 80 seconds by exposure to two oppositely-disposed Visilux 2™ (3M Co., St. Paul, MN) units. Each sample was then irradiated for 90 seconds using a Dentacolor XS unit (Kulzer, Inc., Germany). Cured samples were cut on a diamond saw to form cylindrical plugs 2 mm long. The plugs were stored in distilled water at 37° C. for 24 hours. DTS values for each example was measured using an Instron™ unit (from Instron 4505, Instron Corp. Canton, Massachusetts) with a 10kN load cell. A total of 3 cylinders of cured material having 2 mm in length and 4 mm in diameter were prepared and tested for each example.

Compressive Strength (CS)

High compressive strength in a dental material is advantageous due to the forces exerted by mastication on dental repairs, replacements and restorations. The inventive material, when hardened, preferably have a compressive strength of at least 35 MPa, more preferably at least 200 MPa, and most preferably at least 350 MPa.

ADA specification No. 27 was followed CS testing. Each example was packed and cured as above in the DTS test method. Cured samples were cut on a diamond saw to form cylindrical plugs 8 mm long. The plugs were stored in distilled water at 37° C. for 24 hours. The compressive strength (CS) of these samples was tested on an Instron™ unit with 10kN load cell. A total of 3 cylinders of cured material having 8 mm length and 4 mm diameter were prepared and tested for each example.

Watts Shrinkage Test

This test measures the volumetric shrinkage of a sample after polymerization. A 120 mg portion of each sample was weighed out. The procedures described in "Determination of Polymerization Shrinkage Kinetics in Visible-Light-Cured Materials: Methods Development" (Dental Materials, October 1991, pgs 281–286) were used to prepare and test the samples with the following exceptions. A 1 mm thick brass ring was used. Output signals were acquired through an analog-to-digital converter in a microcomputer using LabView (National Instruments, Bridgeview TX) automation software. Each sample was cured for 60 seconds with a Visilux 2™ (3M, St. Paul, Minn.) with data collection starting at the time of cure and continuing during 5 minutes of post-cure. Three replicates were performed for each sample.

Toothbrush Abrasion Resistance Test

A rectangular 20×9×3 mm thick paste of each example was cured with a Visilux 2™ unit for 80 seconds followed by additional curing for 90 seconds in a Dentacolor™ XS light box (Kulzer, Inc., Germany). Samples were mounted with double sized adhesive tape (Scotch Brand Tape, Core series 2-1300, St. Paul, Minn.) to a holder. The mounted examples were polished according to the following procedure where a series of steps were performed sequentially as shown in the Table 1, using a Buehler ECOMET 4 Polisher with an AUTOMET 2 Polishing Head.

TABLE 1

POLISHING STEPS

| Step# | Abrasive | Grit | Lubricant | RPM | Rotation | Load (lbs) per sample | Time |
|---|---|---|---|---|---|---|---|
| 1 | SiC | 320 | Water | 150 | Clockwise | 1 | 0:40 |
| 2 | Rinse | | Water | | | | |
| 3 | SiC | 600 | Water | 150 | Clockwise | 1 | 1:00 |
| 4 | Rinse | | Water | | | | |
| 5 | 9 mm diamond paste | 9 mm diamond. | Oil | 130 | Clockwise | 1 | 2:00 |
| 6 | Rinse | | Water, soapy water, isopropanol | | | | |
| 7 | 3 mm diamond paste | 3 mm diamond | Oil | 130 | Clockwise | 1 | 2:00 |
| 8 | Rinse | | Water, soapy water, isopropanol | | | | |
| 9 | Master Polish Solution | Master Polish | Water | 120 | Clockwise | 0.75 | 1:40 |
| 10 | Rinse | | Water, soapy water, isopropanol | | | | |

A micro-tri-gloss instrument (BYK Gardner, Columbia, Md.) was used to collect photoelectric measurements of specularly reflected light from the sample surface after polishing and after toothbrushing. The procedure described in ASTM D 523-89 (Reapproved 1994) Standard Test Method for Specular Gloss, for measurements made at 60° geometry was followed with the following modification. Initial gloss after polishing ($G_I$) was measured for initial sample. Final gloss after 500 toothbrushing cycles ($G_F$) was measured. A $\Delta G$ value was calculated with the following formula: $\Delta G = (G_F) - (G_I)$. Randomly selected areas on the rectangular sample was measured for initial and final gloss. Each sample was brushed for a total of 500 cycles with an ORAL B™ 40 medium Straight toothbrush (Oral B Laboratories, Belmont, Calif.) using CREST™ Regular Flavor (Proctor & Gamble, Cincinnati, OH) toothpaste. One operator brushed all the samples using forces on the order of toothbrushing forces. Each sample was brushed with the same toothbrush. One toothbrushing cycle was a forward and a back stroke.

Three-Body Wear Testing

The wear rate of the cured samples was determined by an in-vitro 3-body wear test using a Davidson Wear Tester Model 2 (ACTA, Amsterdam) unit. The Davidson Wear Tester was calibrated to ensure that the wear track was perpendicular to the wheel face. Uncured samples (constituting the first body) were loaded into a 10 mm by 4 mm slot on a 47.75mm diameter wear wheel of the Davidson Wear Tester. The samples were cured for 80 seconds using a Visilux 2™ Curing Light (3M Co., St. Paul, Minn.). The wear wheel, with the cured samples mounted, measured 50.80 to 53.34 mm in diameter. The cured samples on the wear wheel were machined smooth using a Carter Diamond Tool device (S-2192 SYN, Carter Diamond Tool Corp., Willoughby, Ohio) turning at 900 rpm. Water was flooded onto the wheel to control dust and to dissipate heat during the machining process.

The finial diameter of the first body wear wheel was 48.26mm ±0.254 to 0.381 mm. During testing, the first body was allowed to contact another wheel (constituting the second body), that acted as an antagonistic cusp. During contact, the two wheels were immersed in a slurry (constituting the third body:) having 150 grams of ground and filtered bird seed (Wild Bird Mix, Greif Bros. Corporation, Rosemount, Minn.), 25 grams of polymethyl methacrylate (QuickMOUNT Powder Ingredient, Fulton Metallurgical Products Corp., Valencia, Pa.), and 275 ml of water. The two wheels were counter-rotated against each other for 166,000 cycles. Dimensional loss during these cycles was measured every 39,000 cycles by a Perthometer PRK profilometer (Feinpruef Corp., Charlotte, N.C.) along the 10 mm face of the cured and machined composite. Data was collected in a Wear Version 3 software (ACTA, Amsterdam). The data was plotted using linear regression and the wear rates for the samples were determined by calculating the slope of the lines. The wear rate for each sample was reported as a change in unit length per number of cycles (e.g., mm/cycle) and then normalized to the wear rate of a standard material, which was selected to be Z250™ composite (3M Co., St. Paul, Minn.). Thus, the wear resistance in Table 4 is a dimensionless value. There were three replications per sample.

Abbreviations/Definitions

| Abbreviations as used in Examples | Description and/or Trade Name | Supplier |
|---|---|---|
| BISEMA6 | Ethoxylated (6 mole ethylene oxide) bisphenol A dimethacrylate | Sartomer CD541 (Union Carbide) |
| UDMA | diurethane dimethacrylate, CAS No. 41137-604, which is commercially available as Rohamere 6661-0 | Rohm Tech, Inc. (Malden, MA) |
| BisGMA | 2,2-bis[4-(2-hydroxy-3-methacryloyloxy-propoxy)phenyl]propane | |
| TEGDMA | triethyleneglycol dimethacrylate | |
| CPQ | camphorquinone | |
| DPI PF6 | diphenyl iodonium hexafluorophosphate | |
| EDMAB | ethyl 4-dimethylaminobenzoate | |
| BHT | 2,6-Di-tert-butyl-4-methylphenol | |
| BHMPA | 2,2-bis(hydroxymethyl)propionic acid | |
| MEEAA | (2-[2-(2-methoxy)ethoxy]ethoxy acetic acid) | |
| THF | tetrahydrofuran | |
| Norbloc 7966 | (CAS 96478-09-0) 2-(2'-Hydroxy-5'-methacryloxyethylphenyl)-H-benzotriazole | Janssen Pharmaceutica |
| Tinuvin-P | 2-(2H-Benzotriazol-2-yl)-4-methylphenol | Ciba-Geigy |
| TFAA | trifluoroacetic acid | Aldrich (Milwaukee, WI) |
| Styrylsilane | styrylethyltrimethoxysilane, 95% | Gelest Inc. (Tullytown, PA) |

Abbreviations/Definitions

| Abbreviations as used in Examples | Description and/or Trade Name | Supplier |
|---|---|---|
| A174 | γ-methacryloxypropyl-trimethoxysilane | Witco Osi Specialties (Danbury, CT) |
| Nalco 1042 | colloidal silica sol containing 33–36% solids, a nitric acid stabilized colloidal silica sol with a pH of 3.2 | Nalco (Naperville, IL) |
| Nalco 2329 | aqueous colloidal silica containing 40 wt % $SiO_2$, sodium counter ion, pH = 8.4 at 25° C., 75 nm particle size | Nalco (Naperville, IL) |
| Nalco 2326 | aqueous colloidal silica containing 15 wt % $SiO_2$, pH = 9.0 at 25° C., 5 nm particle size, ammonium stabilized | Nalco (Naperville, IL) |
| Nalco 2327 | aqueous colloidal silica containing 40 wt % $SiO_2$, pH = 9.3 at 25° C., 20 nm particle size, ammonium stabilized | Nalco (Naperville, IL) |
| Zirconia Sol | aqueous zirconia sol containing 33 wt % $ZrO_2$, made according to U.S. Pat. No. 5,037,579 (Matchette) | Nalco (Naperville, IL) |
| Methoxy Propanol | 1-methoxy-2-propanol | Aldrich (Milwaukee, WI) |
| Master Polish | slurry solution | Buehler Ltd. Lake Bluff, IL |
| MEI zirconyl acetate | zirconyl acetate | Magnesium Elektron, Inc. (Flemington, NJ |

Resin Component

The following components were used to make the hardenable resin, which was used in Examples 1 to 10 and Comparative Examples A to E. PBW means parts by weight.

TABLE 2

| Constituents | PBW |
|---|---|
| bis-GMA | 24.18% |
| UDMA | 33.85% |
| bis-EMA6 | 33.85% |
| TEGDMA | 4.84% |
| CPQ | 0.2% |
| DPIHFP | 0.5% |
| EDMAB | 1.0% |
| BHT | 0.1% |
| Norbloc 7966 | 1.5% |

Nano-sized particle filler, Type #1

Nalco 2329 silica sol was silane treated as follows to yield nano-sized silica particles. Into a first beaker was charged 450 g Nalco 2329. Into a second beaker was charged 450 g methoxy-2-propanol, 2.976 g A174 (0.15 mmol/g), and 3.199 g styrylsilane. The alcohol solution was thoroughly mixed. The alcohol solution was added to the silica sol slowly with mixing (5 minutes). The resultant mixture was reacted at 80° C. for 16 hr to produce a modified silica sol. Water was added to the modified silica sol to achieve a minimum water to alcohol ratio of 4:1. This mixture was spray-dried using a Buchi spray drier at 200° C inlet temperature and 85° C. to 1 00° C. outlet temperature.

Nanosized particle filler, Type #2

Nalco 2327 silica sol was silane treated according to the procedures set forth above for Nalco 2329 except that 175 g Nalco 2327, 196.9 g methoxy-2-propanol, and 10.78 g of A174 (0.62 mmol/g) were used.

Nano-sized particle filler, Type #3

Nalco 2326 was silane treated according to the procedures set forth above for Nalco 2329, except that 233.34 g Nalco 2326, 262.55 g methoxy-2-propanol, and 19.74 g A174 (2.24 mmol/g) were used.

Nano-sized particle filler, Type #4

Nano-sized particle having zirconia chemical constituent was made as follows. Thoroughly mixed 14.95 g of MEEAA and 210 g of Zirconia Sol made according to U.S. Pat. No. 5,037,579 for 2 minutes in a beaker. A solution containing 23.46 g of PAMA (described below) and 25 g of ethanol was added to the beaker. The contents were mixed thoroughly using a magnetic stir bar for 60 minutes followed by spray drying using a Buchi spray drier at 200° C. inlet temperature and 85° to 100° C. outlet temperature. The solids were collected as filler particles.

PAMA, which is 2-hydroxymethyl-2-[(N-methacryloxyethyl) carbamoylmethyl] propionic acid, a surface treating agent, was made as follows. Into a reactor was charged an excess amount of BHMPA (139.94 g, 1.043 mole), BHT (0.2322 g, 1.054 mmole), triphenyl antimony (0.1891 g, 0.536 mmole), and dibutlytin dilaurate (0.6801 g, 1.077 mmole). The BHMPA was only slightly soluble in THF at room temperature. Isocyanatoethylmethacrylate (IEM) was gradually dripped (80.94 g, 0.522 mole) into the above mixture. The reaction occured at 60° C. for 24 hours with constant mixing. At the end of the reaction and after the solution was cooled down, most of the unreacted BHMPA settled out as white solid powder. Unreacted BHMPA was filtered off by vacuum filtration, and the solvent was then stripped off. The recovered BHMPA could be used in future reactions.

After the removal of the solvent, the product was slightly cloudy due to slow precipitation of residual BHMPA. Enough diethyl ether was added to dissolve the product and then the solution was allowed to sit overnight (approximately 18 hours) undisturbed to precipitate out most of the remaining BHMPA in solution. The white precipitate was filtered off by vacuum filtration, and diethyl ether was removed.

The resulting PAMA was a colorless, flowable liquid. The purity of PAMA in the final product was approximately 80% by molar ratio, with 2,2-di(N-methacryloxyethyl carbamoylmethyl) propionic acid (PDMA) being the main side-product (approximately 17%) and small amounts of remaining BHMPA (approximately 3%).

Cluster particles filler

A 5.0 kg portion of Nalco 1042 sol was weighed out, and the pH of the sol was adjusted to 2.5 using dilute nitric acid. The pH-adjusted sol was added slowly to 2.95 kg of MEI zirconyl acetate and stirred for 1 hour. This mixture was then spray-dried using a 3-foot Niro Spray Drier (Niro 3-foot Mobile Minorm Spray Drier, Columbia, Maryland) at 325° C. inlet temperature and 120° C outlet temperature. The resulting filler was heat-treated (calcined) at 550° C. for 4 hours. The calcined filler was ball-milled for 160 hours to achieve an average cluster size of 1 micron.

The clusters made above were surface treated as follows. To a 20 g portion of the prepared cluster filler was added 40 g of deionized water followed by thorough mixing with a magnetic stir bar for two minutes to yield a homogenous mixture. The pH of the solution was adjusted to 8.5 with ammonium hydroxide. A 1.7g amount of Al 74 was then added. The contents were mixed thoroughly using a magnetic stir bar for 120 minutes and then the final pH is adjusted to 8.25. The reaction mixture was spray-dried using a Buchi spray drier (Buchi/Brinkmann Mini Spray Dryer Model 190, Brinkmann Instruments, Inc. Westbury, N.Y.) at 200° C. inlet temperature and 85° C. outlet temperature.

EXAMPLES 1 to 8

Dental pastes for Examples 1 to 8 and Comparative Examples A to D were prepared by thoroughly mixing together resin (components listed in Table 2) and various filler components as shown in Table 3, which lists the amounts of each component in grams. The pastes were debubbled for approximately 16 hours at 45° C.

TABLE 3

CONSTITUENTS AND AMOUNTS OF VARIOUS EXAMPLES

| Examples | Nano-sized particles | | | Clusters | Resin |
|---|---|---|---|---|---|
| | Type 1 | Type 2 | Type 3 | | |
| 1 | — | 9.1 | — | 70.9 | 20 |
| 2 | — | 16.7 | — | 65 | 18.3 |
| 3 | — | — | 6.7 | 78.7 | 14.6 |
| 4 | — | — | 13.3 | 72 | 14.7 |
| 5 | — | — | 20 | 65.3 | 14.7 |
| 6 | — | 11.5 | 6.3 | 64.8 | 17.4 |
| 7 | — | 27.3 | — | 52.7 | 20 |
| 8 | — | 18.2 | — | 61.8 | 20 |
| Comp A | — | — | — | 80 | 20 |
| Comp B | — | — | — | 82.1 | 17.9 |
| Comp C | 66.7 | 8.3 | — | — | 25 |
| Comp D | 71.7 | — | — | — | 28.3 |

The clusters used in these examples came from a first batch. Examples 1, 2, 7, and are similar in that they contain nano-sized particles, Type #2 (silica, 20 nm) and clusters, but in varying amounts of each filler type. Examples 3, 4, and 5 are similar in that they contain nano-sized particles, Type #3. (silica, 5 nm) and clusters, but in varying amounts of each filler type. Example 6 contained two type of nano-sized particles, Type #2 and #3, in combination with the clusters.

In contrast, Comparative Examples A and B contain only cluster type fillers and Comparitive Examples C and D contain only nano-sized particle fillers.

Various ous tests were done on these examples, and the data is reported in Table 4.

TABLE 4

RESULTS OF VARIOUS PHYSICAL PROPERTIES

| Examples | DTS (psi) | CS (psi) | Gloss ΔG | Watts shrinkage (%) | Wear Resistance |
|---|---|---|---|---|---|
| 1 | 12,900 | 64,000 | −31.6 | −2.06 | 0.549 |
| 2 | 12,600 | 69,200 | −27.4 | −1.90 | NR |
| 3 | 10,800 | 58,000 | −40.0 | −1.54 | 0.576 |
| 4 | 10,800 | 66,200 | −24.2 | −1.66 | 0.329 |
| 5 | 10,600 | 59,600 | −22.1 | −1.73 | 0.250 |
| 6 | 12,500 | 63,900 | −38.5 | −1.54 | NR |
| Comp. A | 10,800 | 57,700 | NR | NR | 0.805 |
| Comp. B | 12,900 | 58,700 | −42.9 | −2.17 | NR |
| Comp. C | 13,300 | 74,200 | NR | NR | 0.901 |
| Comp. D | 14,100 | 70,500 | −4.2 | −2.76 | 1.134 |

NR = not run.

The data in Table 4 show that the inventive samples, as embodied in Examples 1 to 6, showed, less shrinkage than the comparative examples. The smaller the Watts shrinkage value, the less the sample shrink after cure. One skilled in the art will recognize that change on the order of 0. 1% shrinkage can significantly impact the performance of a dental material. Examples 1 to 6 also showed better wear resistance than the comparative examples. The smaller the wear resistance value, the less the samples were abrated in the three body wear test. In general, Examples 1 to 6 had retained gloss adequately, i.e., they had good polishability. While Comparative D had retained its gloss, when compared to all the examples in Table 4, it had the highest shrinkage and wear resistance values.

The data indicate that dental materials using only clusters as fillers, i.e., Comparative A and B, produced materials that have higher loss in gloss, higher shrinkage, and higher wear, when compared to inventive material, which used combination of clusters and nano-sized particles as fillers. Furthermore, dental materials using only nano-particles as fillers, i.e., Comparative C and D, produced materials that, while having good gloss retention, had very high shrinkage and very poor wear resistance, when compared to the inventive dental material, which used a combination of clusters and nano-sized particles. Thus, it is the combination of clusters and nano-sized particles that impart synergistic effect of better polishability, lower shrinkage, and better wear resistance to the inventive material.

Wear resistance testing was done on Examples 7 and 8. Examples 1, 7, and 8 show that in a system that uses clusters and nano-sized particles as fillers, increasing the amount of nano-sized particles Type #2 decreasing the amount of clusters, while maintaining the amount of resin constant (at 20 grams), produced dental materials that had better wear resistance. The wear resistance data was 0.549, 0.490, and 0.386 for Examples 1, 8, and 7, respectively. These samples had 9.1, 18.2, and 27.3 g of nano-sized particle, Type #2 filler, respectively.

EXAMPLES 9 to 10 AND COMPARITIVE E

Dental pastes for these examples were prepared by thoroughly mixing the resin (components listed in Table 2) and various filler components, as shown in Table 5. The pastes were debubbled for approximately 16 hours at 45° C. Although the clusters used in these examples were made to the procedure set forth in the "Cluster particle fillers" description above, they were made in a second batch. No clusters from the first batch (used for Examples 1 to 8 and Comparatives A to D) were used in Examples 9, 10, and Comparative E. The amounts of fillers and resin in Table 5 are reported in grams.

TABLE 5

| | Example 9 | Example 10 | Comp E |
|---|---|---|---|
| Nano-sized particles Type 2 | 9.1 | 9.2 | — |
| Nano-sized particles Type 4 | — | 3.3 | — |
| Clusters | 70.9 | 67.8 | 78.0 |
| Resin | 20.0 | 20.0 | 22.0 |
| Results: | | | |
| DTS (psi) | 11,900 | 11,700 | 11,300 |
| CS (psi) | 58,900 | 54,600 | 52,800 |
| Gloss, ΔG | −18.1 | −27.6 | −42.1 |
| Watt shrinkage (%) | −2.0 | NR | −2.11 |
| Wear resistance | 0.528 | 0.663 | 0.689 |
| Visual opacity | 0.35 | 0.26 | 0.15 |

NR = not run

The data in Table 5 shows that Comparative E contained only cluster type filler particles and had low visual opacity of 0.15. When a combination of clusters and nano-sized particles Type #2 (silica, 20 nm) was used, as in Example 9, the visual opacity increased to 0.35. When a combination of clusters, nano-sized particles Type #2 and Type #4 (zirconia) was used, as in Example 10, the visual opacity was reduced to 0.26. Thus, there was a benefit in visual opacity of using nano-sized particle fillers having non-heavy metal oxide particles and heavy metal oxide particles.

While Comparative E had low visual opacity, it had higher loss in gloss, higher shrinkage, and was not as wear resistant, compared to Examples 9 and 10.

All references cited herein, including patents, patent applications, are incorporated herein by reference in their entirety.

What is claimed is:

1. A material comprising:
    (a) a hardenable resin; and
    (b) a filler comprising (i) clusters of nano-sized particles, said clusters comprising non-heavy metal oxide particles and heavy metal oxides and being not fully densified and (ii) non-agglomerated nano-sized particles selected from the group consisting of non-heavy metal oxide particles, heavy metal oxide particles, and combinations thereof,
    wherein said material is a dental material.

2. The material of claim 1, wherein said non-heavy metal oxide particles are selected from the group consisting of silica, titanium dioxide, aluminum oxide, and combinations thereof.

3. The material of claim 1, wherein said heavy metal oxide comprises a heavy metal having an atomic number greater than 30.

4. The material of claim 1, wherein said heavy metal oxide is selected from the group consisting of zirconium oxide, cerium oxide, tin oxide, yttrium oxide, strontium oxide, barium oxide, lanthanum oxide, zinc oxide, ytterbium oxide, bismuth oxide, and combinations thereof.

5. The material of claim 1, wherein said clusters have an average diameter of less than about 1 micrometer.

6. The material of claim 1, wherein said non-agglomerated nano-sized particles have an average diameter of less than about 100 nanometers.

7. The material of claim 1, wherein said filler comprises at least about 60% by weight of said clusters and at most about 40% by weight of said nano-sized particles, based on the total filler.

8. The material of claim 1, wherein said hardenable resin is selected from the group consisting of acrylates, methacrylates, epoxies, and combinations thereof.

9. The material of claim 1, wherein said material is selected from the group consisting of dental resotratives, dental adhesives, dental mill blanks, dental cements, dental prostheses, orthodontic devices and adhesives, dental casting materials, and dental coatings.

10. The material of claim 1, wherein the material, after hardening, has a visual opacity of less than about 0.35 as measured on a MacBeth transmission densitometer Model TD-903.

11. A method of making a dental material comprising:
    providing a hardenable resin;
    providing a filler comprising (i) clusters of nano-sized particles, said clusters comprising non-heavy metal oxide particles and heavy metal oxides and being not fully densified and (ii) non-agglomerated nano-sized particles selected from the group consisting of non-heavy metal oxide particles, heavy metal oxide particles, and combinations thereof;
    surface treating said filler to yield surface-treated filler particles; and
    mixing said surface treated filler particles with said hardenable resin.

12. The method of claim 11, wherein said non-heavy metal oxide particles are selected from the group consisting of silica, titanium dioxide, aluminum oxide, and combinations thereof.

13. The method of claim 11, wherein said heavy metal oxide comprises a heavy metal having an atomic number greater than 30.

14. The method of claim 11, wherein said heavy metal oxide is selected from the group consisting of zirconium oxide, cerium oxide, tin oxide, yttrium oxide, strontium oxide, barium oxide, lanthanum oxide, zinc oxide, ytterbium oxide, bismuth oxide, and combinations thereof.

15. The method of claim 11, wherein said clusters have an average diameter of less than about 1 micrometer.

16. The method of claim 11, wherein said non-agglomerated nano-sized particles have an average diameter of less than about 100 nanometers.

17. The method of claim 11, wherein said filler comprises at least about 60% by weight of said clusters and at most about 40% by weight of said nano-sized particles, based on the total filler.

18. The method of claim 11, wherein said hardenable resin is selected from the group consisting of acrylates, methacrylates, epoxies, and combinations thereof.

19. The method of claim 11, wherein said dental material is selected from the group consisting of dental resotratives, dental adhesives, dental mill blanks, dental cements, dental prostheses, orthodontic devices and adhesives, dental casting materials, and dental coatings.

20. The method of claim 11, wherein said dental material, after hardening, has a visual opacity of less than about 0.35 as measured on a MacBeth transmission densitometer Model TD-903.

21. A method of using a dental material comprising:
    placing the material near or on a tooth surface;
    changing the topography of the material; and
    hardening the material, wherein the dental material comprises a hardenable resin and a filler comprising (i) clusters of nano-sized particles, said clusters comprising non-heavy metal oxide particles and heavy metal oxides and being not fully densified and (ii) non-agglomerated nano-sized particles selected from the group consisting of non-heavy metal oxide particles, heavy metal oxide particles, and combinations thereof.

22. The method of claim 21, wherein placing, changing, and hardening are performed sequentially.

23. The method of claim 21 further comprising finishing the surface of the hardened material.

24. The method of claim 21 wherein the hardened material forms a dental article selected from the group consisting of dental mill blanks, dental prostheses, orthodontic devices, artificial crowns, anterior fillings, posterior fillings, and cavity liners.

25. A dental article preparable by a method comprising:
    hardening a dental material comprising a hardenable resin and a filler comprising (i) clusters of nano-sized particles, said clusters comprising non-heavy metal oxide particles and heavy metal oxides and being not fully densified and (ii) non-agglomerated nano-sized particles selected from the group consisting of non-heavy metal oxide particles, heavy metal oxide particles, and combinations thereof; and
    fabricating a dental article selected from the group consisting of dental mill blanks, dental prostheses, orthodontic devices, artificial crowns, anterior fillings, posterior fillings, and cavity liners.

* * * * *

UNITED STATES PATENT AND TRADEMARK OFFICE
CERTIFICATE OF CORRECTION

PATENT NO.   : 6,572,693 B1
DATED        : June 3, 2003
INVENTOR(S)  : Wu, Dong

It is certified that error appears in the above-identified patent and that said Letters Patent is hereby corrected as shown below:

Title page,
Item [57], ABSTRACT,
Line 3, delete "beavy" and insert -- heavy --, therefor.
Item [56], References Cited, FOREIGN PATENT DOCUMENTS, delete "EP" and insert -- DE --, therefor.
OTHER PUBLICATIONS, "Definition of "Binary Compound," reference, delete "201" and insert -- © --, therefor.

Column 2,
Line 41, delete "beavy" and insert -- heavy --, therefor.
Lines 47-54, delete "In brief summary... dental material." (Paragraph repeated).
Line 57, delete "(i)-clusters" and insert -- (i) clusters --, therefor.
Lines 66-68, delete "A method of making the inventirve dental material comprises the acts of: (a) providing a hardenable resin; (b)" (Paragraph repeated).

Column 3,
Lines 1-9, delete "providing a powder... hardenable resin." (Paragraph repeated).

Column 4,
Line 62, after "non-heavy" delete "to".

Column 13,
Line 42, delete "1,1 0" and insert -- 1,10 --, therefor.

Column 16,
Line 59, delete "denial" and insert -- dental --, therefor.

Column 17,
Line 5, after "blanks", insert -- . --
Line 58, delete "preferably 05" and insert -- preferably 0.05 --, therefor.

Column 19,
Line 63, delete "body:" and insert -- body. --, therefor.

Column 20,
Line 48, delete "604" and insert -- 60-4 --, therefor.

UNITED STATES PATENT AND TRADEMARK OFFICE
CERTIFICATE OF CORRECTION

PATENT NO. : 6,572,693 B1
DATED : June 3, 2003
INVENTOR(S) : Wu, Dong

It is certified that error appears in the above-identified patent and that said Letters Patent is hereby corrected as shown below:

Column 21,
Line 63, delete "Nanosized" and insert -- Nano-sized --, therefor.

Column 22,
Line 53, delete "Minorm" and insert -- Minor$^{TM}$ --, therefor.
Line 63, delete "Al 74" and insert -- A174 --, therefor.

Column 23,
Line 31, after "and" insert -- 8 --.
Line 40, delete "Comparitive" and insert -- Comparative --, therefor.

Signed and Sealed this

Second Day of November, 2004

JON W. DUDAS
*Director of the United States Patent and Trademark Office*

UNITED STATES PATENT AND TRADEMARK OFFICE
CERTIFICATE OF CORRECTION

PATENT NO. : 6,572,693 B1  
APPLICATION NO. : 09/698986  
DATED : June 3, 2003  
INVENTOR(S) : Dong Wu et al.

Page 1 of 1

It is certified that error appears in the above-identified patent and that said Letters Patent is hereby corrected as shown below:

Title Page (Related U.S. Application Data)

Item (63)  Delete "Continuation-in-part of application No. 09/428,830, filed on Oct. 28, 1999, now abandoned, which is a continuation-in-part of application No. 09/429,185, filed on Oct. 28, 1999, now Pat. No. 6,387,981, which is a continuation-in-part of application No. 09/428,937, filed on Oct. 28, 1999, now abandoned, which is a continuation-in part of application No. 09/428,374, filed on Oct. 28, 1999, now Pat. No. 6,376,590." and insert -- Continuation-in-part of application No. 09/428,830, filed on Oct. 28, 1999, now Pat. No. 6,730,156; Continuation-in-part of application No. 09/429,185, filed on Oct. 28, 1999, now Pat. No. 6,387,981; Continuation-in-part of application No. 09/428,937, filed on Oct. 28, 1999, now abandoned; and Continuation-in-part of application No. 09/428,374, filed on Oct. 28, 1999, now Pat. No. 6,376,590. --, therefor.

Signed and Sealed this

Seventeenth Day of March, 2015

Michelle K. Lee
*Director of the United States Patent and Trademark Office*